(12) United States Patent
Bjørsvik

(10) Patent No.: US 7,528,271 B2
(45) Date of Patent: May 5, 2009

(54) INTERMEDIATES, PROCESS FOR THEIR PREPARATION AND SYNTHESIS OF 1,4-BENZOQUIONES

(75) Inventor: Hans-René Bjørsvik, Bergen (NO)

(73) Assignee: Bergen Teknologioverforing AS, Bergen (NO)

( * ) Notice: Subject to any disclaimer, the term of this patent is extended or adjusted under 35 U.S.C. 154(b) by 0 days.

(21) Appl. No.: 11/798,749

(22) Filed: May 16, 2007

(65) Prior Publication Data

US 2008/0287702 A1    Nov. 20, 2008

(51) Int. Cl.
C07C 50/04    (2006.01)
C07C 43/00    (2006.01)
C07C 69/76    (2006.01)

(52) U.S. Cl. .................. 552/293; 560/61; 568/630; 568/650

(58) Field of Classification Search .............. 552/293; 560/61; 568/630, 650
See application file for complete search history.

(56) References Cited

U.S. PATENT DOCUMENTS

| 4,062,879 | A | * | 12/1977 | Kijima et al. | ............... | 552/307 |
| 4,559,177 | A | * | 12/1985 | Okutani et al. | .............. | 552/307 |
| 4,952,712 | A | * | 8/1990 | Orita et al. | ................. | 552/307 |
| 4,992,469 | A | * | 2/1991 | Ozawa et al. | ............... | 514/559 |

OTHER PUBLICATIONS

Huther et al. Radical Reaction Using Decacarbonyldimanganese under Bisphasic Conditions. European Journal of Organic Chemistry. 2004, pp. 1740-1749.*

Matsumoto et al. Hexacyanoferrate-Catalyzed Oxidation of Trimethoxybenzenes to Dimethoxy-p-benzoquinones with Hydrogen Peroxide. Journal of Organic Chemistry. 1985, vol. 50, pp. 1766-1768.*

* cited by examiner

*Primary Examiner*—Sikarl A Witherspoon
(74) *Attorney, Agent, or Firm*—Reed Smith LLP; Juan Carlos A. Marquez, Esq.

(57) ABSTRACT

The present invention discloses a new process for the preparation of 1,4-benzoquiones of formula (II)

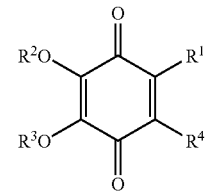

(II)

wherein $R^1$, $R^2$, $R^3$ and $R^4$ are independently selected from the group consisting of branched or unbranched $C_1$-$C_6$ alkyl, phenyl and benzyl, wherein phenyl and benzyl is optionally substituted by one or more substituent independently selected from the group consisting of $C_1$-$C_6$ alkyl and halogen, and wherein $C_1$-$C_6$ alkyl is optionally substituted with one or more halogen susbstituents, and wherein $R^2$ and $R^3$ together can form a $C_1$-$C_6$-alkylene radical, optionally substituted by one or more susbstituents independently selected from the group comprising $C_1$-$C_6$, benzyl, phenyl and halogen. One preferred compound is 2,3-dimethoxy-5-methyl-[1,4]benzoquinone, also known as coenzyme $Q_0$ ($CoQ_0$). Also disclosed are novel compounds and intermediates, and a method for the preparation of coenzyme $Q_n$, preferable the coenzyme $Q_{10}$. Also disclosed is a method for continuous synthesis of 1,4-benzoquiones in a continuous flow reactor.

23 Claims, 2 Drawing Sheets

INTERMEDIATES, PROCESS FOR THEIR PREPARATION AND SYNTHESIS OF 1,4-BENZOQUIONES

FIELD OF THE INVENTION

The present invention relates to a process for the preparation of 1,4-benzoquiones, and novel compounds and intermediates. The present invention also relates to a method for the preparation of coenzyme $Q_n$, preferable the coenzyme Q10, and a method for continuous synthesis of 1,4-benzoquiones More specifically, the present invention relates to a new efficient synthesis of 2,3-dimethoxy-5-methyl-[1,4]benzoquinone, also known as coenzyme $Q_0$ ($CoQ_0$). This methodology is being successfully incorporated into the synthesis of higher order ubiquinones, such as coenzyme $Q_{10}$ ($CoQ_{10}$).

BACKGROUND OF THE INVENTION $CoQ_n$, $n \leq 12$ isoprene units, are found in the mitochondrian of every cell of nearly all types of verebrates. The Coenzyme $Q_n$ constitute one of the more important classes of compounds involved in the electron-transfer processes vital for the respiration system of verebrates. The Coenzyme $Q_n$ that contains ten isoprene units (n=10) is the redox carrier used by the human being. $CoQ_{10}$ is a important antioxidant use by the celles to trap free radicals. Studies have shown that $CoQ_{10}$ can exert efficacy in treating patients with mitochondrial disorders, and for the treatment of neurodegenerative diseases such as Parkinson's disease, Huntington's disease and amyotrophic lateral sclerosis.

2,3-dimethoxy-5-methyl-[1,4]benzoquinone of formula (I), also known as coenzyme $Q_0$ ($CoQ_0$) has been been shown to be a valuable building block for the synthesis of coenzymes Qn (with n=1-12)

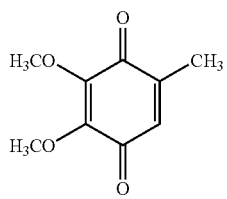

(I)

Previously reported syntheses of the ubiquinones (Moiseenkov, A. M.; Veselovskii, A. B. *Pharm. Chem. J.* 1992, 26, 508) involve multi-step processes, (Anslow, W. K.; Ashley, J. N.; Raistrick, H. *J. Chem. Soc.* 1938, 439. (b) Hoffmann, F. (La Roche Co). Brit. Patent 889704, 1962), require large amounts of oxidizing agents, provide low yields, (Orita, H.; Shimizu, M.; Hayakawa, T.; Takehira, K. (Agency Ind. Sci. Techn., Japan). U.S. Pat. No. 4,952,712, 1990.) and in some cases toxic by-products are formed. (Matsumoto, M.; Kobayashi, H. *J. Org. Chem.* 1985, 50, 1766). In the synthesis of the simplest ubiquinone, $CoQ_0$ (formula I), oxidation of 3,4,5-trimethoxytoluene with various reagents, including Fremy's salt, ceric(IV) ammonium nitrate, $H_2O_2$ in $HCO_2H$, meta-chloroperbenzoic acid or $H_2O_2$ in AcOH, and $H_2SO_4$, give 2,3-dimethoxy-5-methyl-[1,4]benzoquinone in only low yields. Matsumoto and Kobayaski (Matsumoto, M.; Kobayashi, H. *J. Org. Chem.* 1985, 50, 1766) reported the hexacyanoferrate-catalyzed oxidation of 3,4,5-trimethoxytoluene with $H_2O_2$, a more efficient process but still with moderate yields (<50%). Other methods for the synthesis of $CoQ_0$ starting from highly functionalized aromatic starting materials such as vanilline, gallic acid, pyrogallol, and tetramethoxytoluene, are complex multi-step processes. More convenient oxidants, such as molecular oxygen and $H_2O_2$, have attracted considerable attention, although they are generally used in the presence of metal catalysts.

BRIEF SUMMARY OF THE INVENTION

A first object of the present invention is to obtain a process for the preparation of 1,4-benzoquiones of formula (II)

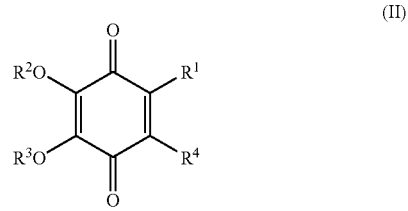

(II)

wherein $R^1$, $R^2$, $R^3$ and $R^4$ are independently selected from the group consisting of branched or unbranched $C_1$-$C_6$ alkyl, phenyl and benzyl, wherein phenyl and benzyl is optionally substituted by one or more substituent independently selected from the group consisting of $C_1$-$C_6$ alkyl and halogen, and wherein $C_1$-$C_6$ alkyl is optionally substituted with one or more halogen susbstituents, and wherein R2 and R3 together can form a $C_1$-$C_6$-alkylene radical, optionally substituted by one or more susbstituents independently selected from the group comprising $C_1$-$C_6$, benzyl, phenyl and halogen, by reacting a compound of formula (III)

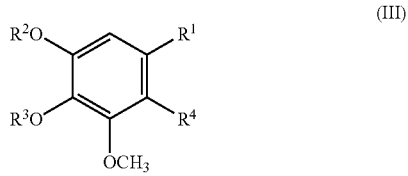

(III)

wherein $R^1$, $R^2$, $R^3$ and $R^4$ are as defined above, with a peroxide oxidant preferable $H_2O_2$, under acidic conditions, preferable in AcOH, with the presence of an acid catalyst such as para-toluenesulfonic acid.

A preferred objective of this aspect is to provide a process for the preparation of 2,3-dimethoxy-5-methyl-[1,4]benzoquinone, also known as coenzyme $Q_0$ ($CoQ_0$), i.e. where R entities of the formula (III) are defined as follows; R1 is methyl, R2 and R3 is methoxy, and R4 is H. This preferred embodiment is starting from 3,4,5-trimethoxytoluene.

Various peroxide oxidizing agents can be used according to the process of the present invention, and the peroxide is preferable selected from the group comprising tert-butylhydrperoxide, cumene hydroperoxide, and hydrogen peroxide, preferable $H_2O_2$.

Various acidic solvents can be used in the process according to the present invention, and the solvent is preferable selected from the group comprising formic acid, acetic acid, propionic acid, preferable AcOH.

Various Brøndsted acids can be used as acid catalyst in the process according to the invention, and the Brøndsted acid is preferable selected from the group comprising sulphuric acid, nitric acid, phosphoric acid, and para-toluensulphonic acid (p-TSA), preferable p-TSA.

An preferred embodiment of process according to the invention further contains the steps of i) cooling the reaction mixture to 0-5° C., preferable over a period of about 10 minutes, and ii) adding $HNO_3$ in order to increase the yield of formula (II).

A further aspect of the present invention relates to novel intermediates of formula (IV),

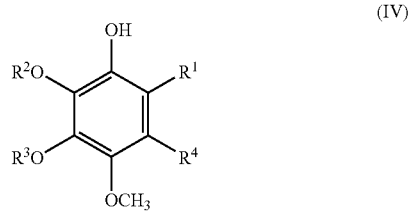

(IV)

wherein $R^1$, $R^2$, $R^3$ and $R^4$ are independently selected from the group consisting of branched or unbranched $C_1$-$C_6$ alkyl, phenyl and benzyl, wherein phenyl and benzyl is optionally substituted by one or more substituent independently selected from the group consisting of $C_1$-$C_6$ alkyl and halogen, and wherein $C_1$-$C_6$ alkyl is optionally substituted with one or more halogen susbstituents, and wherein $R^2$ and $R^3$ together can form a $C_1$-$C_6$-alkylene radical, optionally substituted by one or more susbstituents independently selected from the group comprising $C_1$-$C_6$, benzyl, phenyl and halogen.

A preferred embodiment of this aspect relates to a compound of formula (IV), wherein $R^1$ is methyl, $R^2$ and $R^3$ are methoxy, and $R^4$ is H or a halogen.

A further preferred embodiment of this aspect relates to a compound of formula (IV), wherein $R^1$ is methyl, $R^2$ and $R^3$ are methoxy, and $R^4$ is H.

A further aspect of the invention relates to novel compounds of the formula (V)

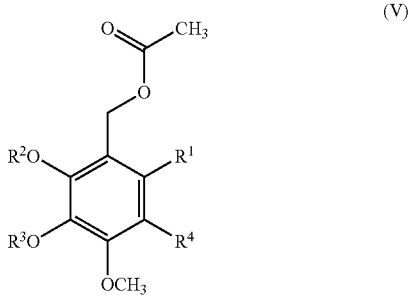

(V)

wherein $R^1$, $R^2$, $R^3$ and $R^4$ are independently selected from the group consisting of branched or unbranched $C_1$-$C_6$ alkyl, phenyl and benzyl, wherein phenyl and benzyl is optionally substituted by one or more substituent independently selected from the group consisting of $C_1$-$C_6$ alkyl and halogen, and wherein $C_1$-$C_6$ alkyl is optionally substituted with one or more halogen substituents, and wherein R2 and R3 together can form a $C_1$-$C_6$-alkylene radical, optionally substituted by one or more substituents independently selected from the group comprising $C_1$-$C_6$, benzyl, phenyl and halogen.

A preferred embodiment of this aspect relates to a compound of formula (V), wherein $R^1$ is methyl, $R^2$ and $R^3$ are methoxy, and $R^4$ is H or a halogen.

A further preferred embodiment of this aspect relates to a compound of formula (V), wherein $R^1$ is methyl, $R^2$ and $R^3$ are methoxy, and R4 is H.

A further aspect of the invention relates to novel compounds of the formula (VI)

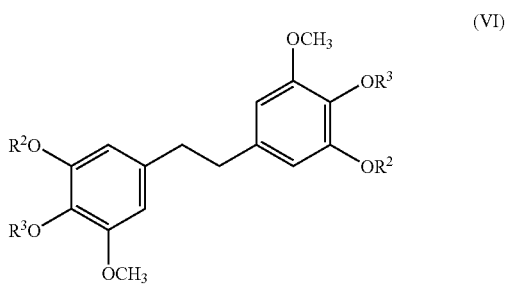

(VI)

wherein $R^2$ and $R^3$ are independently selected from the group consisting of branched or unbranched $C_1$-$C_6$ alkyl, phenyl and benzyl, wherein phenyl and benzyl is optionally substituted by one or more substituent independently selected from the group consisting of $C_1$-$C_6$ alkyl and halogen, and wherein $C_1$-$C_6$ alkyl is optionally substituted with one or more halogen substituents, and wherein $R^2$ and $R^3$ together can form a $C_1$-$C_6$-alkylene radical, optionally substituted by one or more substituents independently selected from the group comprising $C_1$-$C_6$, benzyl, phenyl and halogen.

A further preferred embodiment of this aspect relates to a compound of formula (VI), wherein $R^2$ and $R^3$ are methoxy.

A further aspect of the present invention relates to a process for the synthesis of higher order ubiquinones, i.e. for the preparation of coenzyme $Q_n$ of formula (VII)

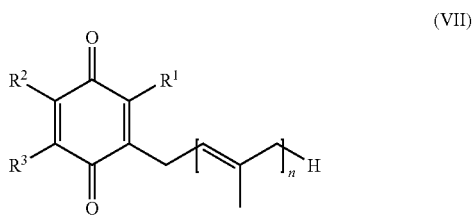

(VII)

wherein a compound of the formula (II), $R^1$, $R^2$, $R^3$ and are as defined above, and $R^4$ is H,

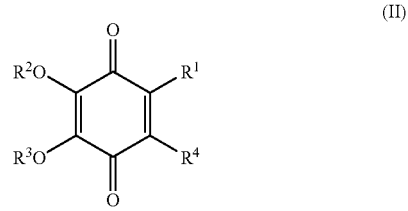

(II)

is prepared by reacting a compound of formula (III)

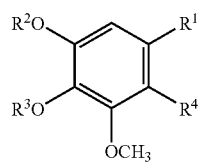
(III)

wherein $R^1$, $R^2$, $R^3$ and $R^4$ are as defined above, with a peroxide oxidant preferable $H_2O_2$, in an acidic solvent, preferable AcOH, with the presence of an acid catalyst such as para-toluenesulfonic acid, and then activating the compound of formula (II) by conventional methods, and coupling of the activated compound of formula (II) with a compound of formula (VIII)

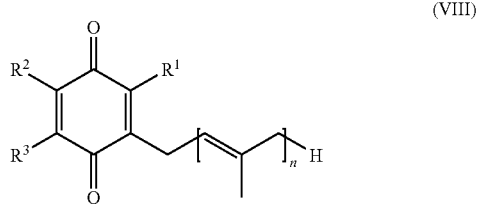
(VIII)

A further aspect of the present invention relates to a method for continuous synthesis of 1,4-benzoquiones, wherein the synthesis takes place in a reactor that encompasses an annular reaction room for supply and outflow of reactants, and where the reactants are fed from one end of the annular reaction room to the other, and thereby are forced through perforations in a number of discs arranged on an oscillator set up so that good mixing is obtained, and where the ratio between "the area of the internal surface of the reaction room" and "the volume of the annular reaction room" is in the area 5-20 $cm^2/cm^3$, preferably about 10 $cm^2/cm^3$, and wherein said 1,4-benzoquiones with the formula (II)

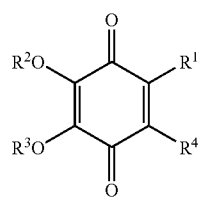
(II)

wherein $R^1$, $R^2$, $R^3$ and $R^4$ are independently selected from the group consisting of branched or unbranched $C_1$-$C_6$ alkyl, phenyl and benzyl, wherein phenyl and benzyl is optionally substituted by one or more substituent independently selected from the group consisting of $C_1$-$C_6$ alkyl and halogen, and wherein $C_1$-$C_6$ alkyl is optionally substituted with one or more halogen substituents, and wherein R2 and R3 together can form a $C_1$-$C_6$-alkylene radical, optionally substituted by one or more substituents independently selected from the group comprising $C_1$-$C_6$, benzyl, phenyl and halogen, is prepared by reacting a compound of formula (III)

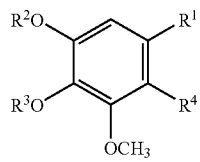
(III)

wherein $R^1$, $R^2$, $R^3$ and $R^4$ are as defined above, with a peroxide oxidant preferable $H_2O_2$, in an acidic solvent, preferable AcOH, with the presence of an acid catalyst such as para-toluenesulfonic acid.

DETAILED DESCRIPTION OF THE INVENTION

Definitions

Figure 1:
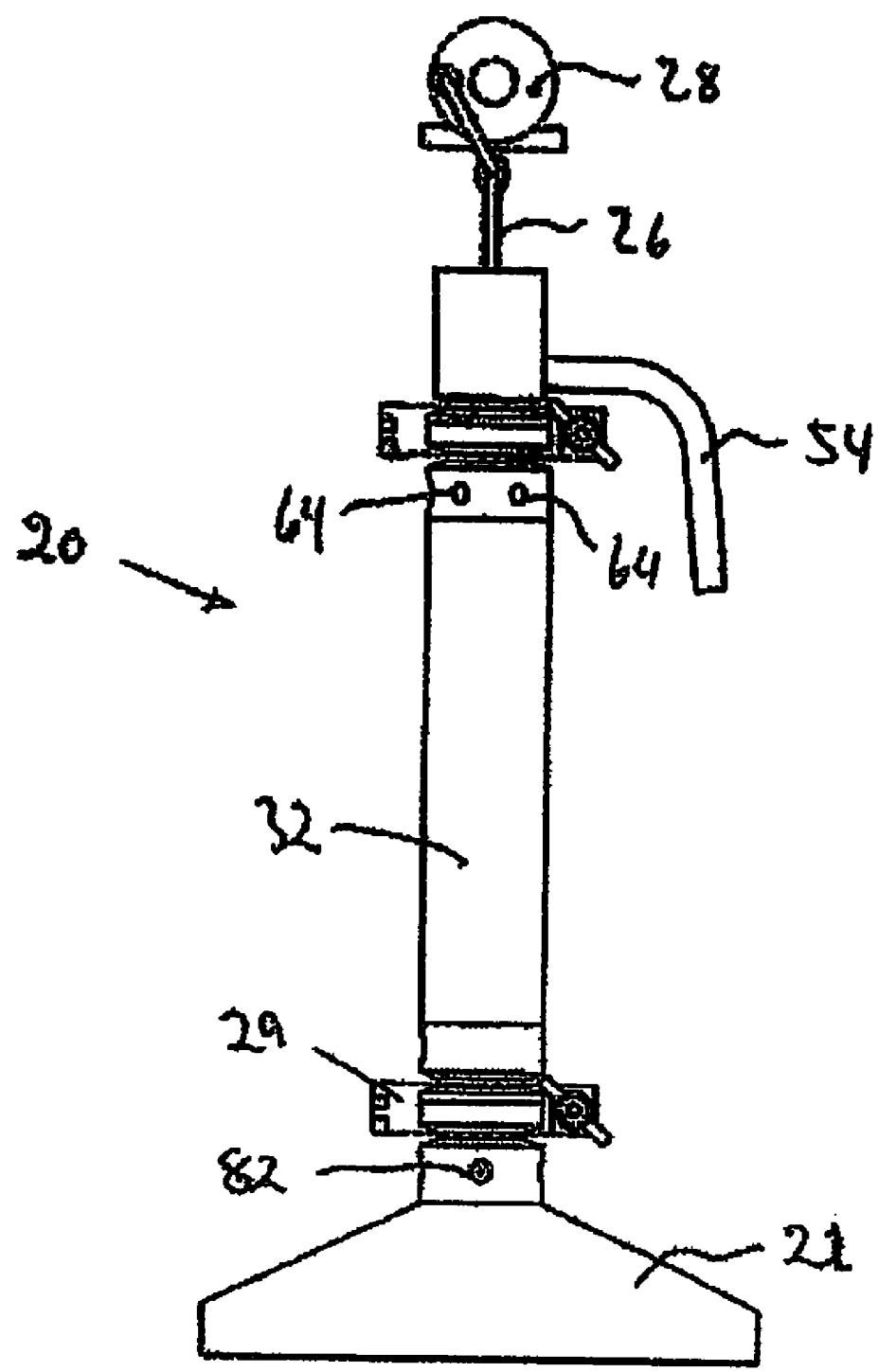
FIG. 1 shows a drawing of an embodiment of a reactor.

As used herein, the term "$C_1$ to $C_6$ alkyl" represents a straight- or branched-chain saturated hydrocarbon containing 1 to 6 carbon atoms which may be unsubstituted or substituted by one or more substituents. Examples of $C_1$ to $C_{12}$ alkyl groups include methyl, ethyl, propyl, 2-propyl, n-butyl, iso-butyl, tert-butyl, pentyl, and the like.

The term "phenyl" as used herein, mean a —$C_6H_5$ group.
The term "benzyl" as used herein, means a —$CH_2C_6H_5$ group.

The term "halogen" refers to fluorine, chlorine, bromine or iodine.

EXPERIMENTAL SECTION

Example 1

Preparation of
2,3-Dimethoxy-5-methyl-[1,4]benzoquinone [$CoQ_0$]

To a round-bottom flask (20 mL) equipped with a reflux condenser was added a solution of commercial 3,4,5-trimethoxy-toluene (0.547 g, 3 mmol) in AcOH (3 mL), followed by para-toluenesulfonic acid monohydrate (57 mg, 0.3 mmol) as catalyst. The oxidant $H_2O_2$ (30%, 0.65 mL, 6 mmol) was then added. The reaction mixture was stirred and heated at 75° C. for 30 min. The resulting dark-red solution was cooled to 0-5° C., and concentrated $HNO_3$ (90%, 1.5 mmol) was then slowly added. The cold solution was poured into $H_2O$ (50 mL) and extracted with $CH_2Cl_2$ (3×50 mL). The combined organic layers were washed with $H_2O$ (80 mL) in order to remove traces of AcOH, dried ($Na_2SO_4$) and filtered. When the solvent was evaporated under vacuum, the final crude (0.528 g, dark-red oil) was dissolved in boiling hexane (70 mL), filtered, and the solvent was removed to give the pure 2,3-Dimethoxy-5- methyl-[1,4]benzoquinone (0.480 g, 88% yield) as red needles. $^1H$ NMR (400 MHz, $CDCl_3$, ppm): $\delta$2.04 [d, 3H, J=1.6 Hz, $CH_3$], 4.00 [s, 3H, $OCH_3$], 4.02 [s, 3H, $OCH_3$], 6.43-6.44 [q, 1H, $J_m$=1.6 Hz]. $^{13}C$ NMR (400 MHz, $CDCl_3$, ppm): $\delta$15.4, 31.1, 61.2, 131.3, 144.0, 144.9, 145.1, 184.1, 184.4. MS m/z (%): 182 (85), 167 (32), 153 (13), 137 (100), 121 (6), 111 (23), 96 (12), 83 (67), 69 (31), 53 (15).

Example 2

Preparation of 3,4,5-Trimethoxybenzyl acetate

To a two-necked round-bottom flask containing a solution of 3,4,5-trimethoxytoluene (0.547 g, 3 mmol) in AcOH (5 mL) was added, by means of a syringe pump (rate=20 mL/h), a 0.32 M solution of $HNO_3$ (65%, 3.2 mmol, 0.222 mL) in AcOH (10 mL) over a period of 30 min at 20° C. The solution was stirred for another 30 min. The reaction was then quenched with anhydrous $Na_2SO_4$ (5 g) to remove possible $H_2O$ generated in the process, filtered and diluted with EtOAc (puriss p.a. $H_2O \leqq 0.05\%$, 30 mL). The organic solution was passed through silica gel, and the solvent was removed under reduced pressure to give a dark-brown oil (0.745 g) containing 3,4,5-trimethoxybenzyl acetate in ~93% yield ($\geqq 90\%$ purity by GC) and traces of 3,3',4,4',5,5'-hexamethoxybibenzyl. (Note: workup under anhydrous conditions). $^1$H NMR (200 MHz, $CDCl_3$, ppm): δ2.11 [s, 3H, $CH_3$] 3.83 [s, 3H, $OCH_3$], 3.86 [s, 6H, 2×$OCH_3$] 5.03 [s, 2H, $CH_2$], 6.60 [s, 2H, ArH]. $^{13}$C NMR (200 MHz, $CDCl_3$, ppm): δ20.7, 55.8, 60.5, 66.3, 105.3, 131.2, 137.6, 153.0, 170.7. MS m/z (%): 240 (100), 225 (3), 198 (40), 181 (68), 169 (16), 155 (7), 148 (7), 138 (6), 123 (10), 109 (3), 95 (7), 77 (4), 43 (13).

Example 3

Preparation of 2-Chloromethyl-3,4,5-trimethoxytoluene

To a two-necked round-bottom flask containing a solution of $(CH_2O)_n$ (0.030 g, 1 mmol) and HCl (37%, 0.5 mL) in AcOH (5 mL) was added, by means of a syringe pump (rate=10 mL/h), a solution of 3,4,5-trimethoxy-toluene (0.182 g, 1 mmol) in AcOH (5 mL) over a period of 30 min at 20° C. The solution was stirred for another 30 min. The mixture was then poured into EtOAc (40 mL) and washed with $H_2O$ (1×40 mL) and a saturated $NaHCO_3$ aqueous solution (3×40 mL). The organic layer was dried ($Na_2SO_4$), filtered, and concentrated in vacuo to give a transparent oil (0.209 g) containing 2-chloromethyl-3,4,5-trimethoxytoluene in 77% yield, and 2,2',3,3',4,4'-hexamethoxy-6,6'-dimethylbiphenyl-methane (23%) as the main by-product. Purification of 2-chloromethyl-3,4,5- trimethoxytoluene by alumina or silica gel chromatography was fruitless since 2-chloromethyl-3,4,5-trimethoxytoluene, in the presence of traces of $H_2O$, reacted to give the corresponding benzyl alcohol. Using the NMR spectra of a pure sample of 2,2',3,3',4,4'-hexamethoxy-6,6'-dimethylbiphenylmethane as reference (see Supporting Information in Appendix E), the characteristic signals of 2-chloromethyl-3,4,5-trimethoxytoluene were detected in the NMR spectra of the final reaction mixture. $^1$H NMR (200 MHz, $CDCl_3$, ppm): δ2.37 [s, 3H, $CH_3$], 3.84-3.96 [9H, 3×$OCH_3$], 4.68 [s, 2H, $CH_2$], 6.52 [s, 1H, ArH]. $^{13}$C NMR (200 MHz, $CDCl_3$, ppm): δ18.7, 38.6, 55.7, 60.6, 61.4, 109.3, 121.9, 133.4, 140.0, 152.2, 153.4. MS m/z (%): 230 (31), 215 (1), 195 (100), 180 (40), 165 (5), 150 (12), 137 (12), 120 (6), 105 (7), 91 (5), 77 (6), 66 (5).

Example 4

Preparation of 3-Chloromethyl-4,5,6-trimethoxy-2-methylphenol (6.14)

A solution of 2-chloromethyl-3,4,5-trimethoxytoluene (0.161 g, 0.7 mmol) and 2,2',3,3',4,4'-hexamethoxy-6,6'-imethylbiphenylmethane (0.047 g, 0.13 mmol) in AcOH (99.8%, 5 mL) was added to a round-bottom flask (20 mL), followed by para-toluenesulfonic acid monohydrate (19 mg, 0.1 mmol) as catalyst. The oxidant $H_2O_2$ (30%, 0.154 mL, 1.4 mmol) was then added. The reaction mixture was stirred at 20° C. for 1 min. The mixture was then poured into EtOAc (40 mL) and washed with $H_2O$ (1×40 mL) and saturated $NaHCO_3$ aqueous solution (3×40 mL). The organic layer was dried ($Na_2SO_4$), filtered, and concentrated in vacuo to give a pale yellow oil (0.219 g) containing 3-chloromethyl-4,5,6-trimethoxy-2-methylphenol in ~70% yield, and 2,2',3,3',4,4'-hexamethoxy-6,6'-dimethylbiphenylmethane (~23% yield) as the main by-product. MS m/z (%): 246 (26), 230 (1), 211 (7), 197 (100), 182 (6), 169 (5), 154 (18), 137 (7), 121 (3), 111 (9), 91 (4), 83 (11).

Example 5

Continuous Synthesis of 2,3-Dimethoxy-5-methyl-[1,4]benzoquinone [CoQ$_0$]

The continuous synthesis took place in a continuous flow reactor as described below, and the retention time was only 30 minutes.

The 3,4,5-trimethoxy toluene (18.2 g, MW 182.21, 0.1 mol), the PTS acid (1.7 g, MW 172.13, 0.01 mol) are dissolved in glacial acetic acid to give a total volume of 50 ml and the solution is connected to the pump 1. The hydrogen peroxide (0.2 mol, MW 34.02, 21.6 ml if $H_2O_2$ at 30% and 17.5 ml if $H_2O_2$ at 35%) diluted to 50 ml with glacial acetic acid is connected to the pump 2. The nitric acid (90%, 0.05 mol, MW 63.02, d 1.49, 3.15 g, 3.5 g solution 90%, 2.35 ml solution 90%) dissolved in acetic acid (to 50 ml) is connected to the pump 3. Pumps 1, 2, 3 were working respectively at 4.95, 4.95, and 9.45 rpm corresponding about at 0.63 ml/min. Isoversinic tubes used had an ID 1 mm. The residence time of the reaction was about 30 min (38 ml volume reactor) and the reaction was performed at 750 C pumping the solutions of the pumps 1 and 2. After 30 min the nitric acid solution was pumped into the second section of the reactor (11 ml, volume reactor) refrigerated with water system.

The reaction mixture is poured in water (about 100 ml) as soon as it is out of the reactor. The colour is intense red. It was necessary to add about 6.5 ml of $H_2O_2$ solution as above prepared due to the final different consume speed of the reagents. About 50 ml of glacial acetic acid was also pumped in the reactor at the end in order to push out all of the reaction solution.

Work-up: The mixture is evaporated at the rotavapor in order to reduce the total volume. 300 ml of water (and 3 g of NaCl) were added and the mixture was extracted with $CH_2Cl_2$ (4×100 ml), dried and the solvent evaporated obtaining a red oil. The red oil was suspended in 400 ml boiling hexane. The soluble phase is separated from the red-black gummy and evaporated under reduced pressure to give 10.7 g of red oil. The yield was 5%.

Example 6-Example 5

Continuous Synthesis of 2,3-Dimethoxy-5-methyl-[1,4]benzoquinone [CoQ$_0$]

The continuous synthesis took place in a continuous flow reactor as described below, and the retention time was only 5 minutes.

3,4,5-Trimethoxy toluene (18.2 g, MW 182.21, 0.1 mol), para-toluene sulphonic acid (1.7 g, MW 172.13, 0.01 mol) are dissolved in glacial acetic acid to give a total volume of 50 ml and the solution is connected to the pump 1. Hydrogen peroxide (0.2 mol, MW 34.02, 21.6 ml if $H_2O_2$ at 30% and 17.5 ml if $H_2O_2$ at 35%) diluted to 50 ml with glacial acetic acid is connected to the pump 1 (second tube). The nitric acid (90%, 0.05 mol, MW 63.02, d 1.49, 3.15 g, 3.5 g solution 90%, 2.35 ml solution 90%) dissolved in acetic acid (to 50 ml) is connected to the pump 2. The pump 1 is pumping approximately 3.8 ml/min for each of the two reagent solutions (total speed flow 7.6 ml/min, i.e. 38 ml reactor volume/5 min RT). Iso-versinic tubes (ID 2 mm) was used on the peristaltic pump. The residence time of the reaction was about 5 min (38 ml volume reactor) and the reaction was performed at 75° C. pumping the solutions of the pumps 1. After 5 min the nitric acid solution was pumped at 3.8 ml/min into the second section of the reactor (11 ml, volume reactor) cooled by a cold water circuit.

About 50 ml of glacial acetic acid was also pumped in the reactor at the end in order to push out all of the reaction solution.

Work-up: similar as in example 5. The yield was 20%.

Continuous Flow Reactor

Figure 2:
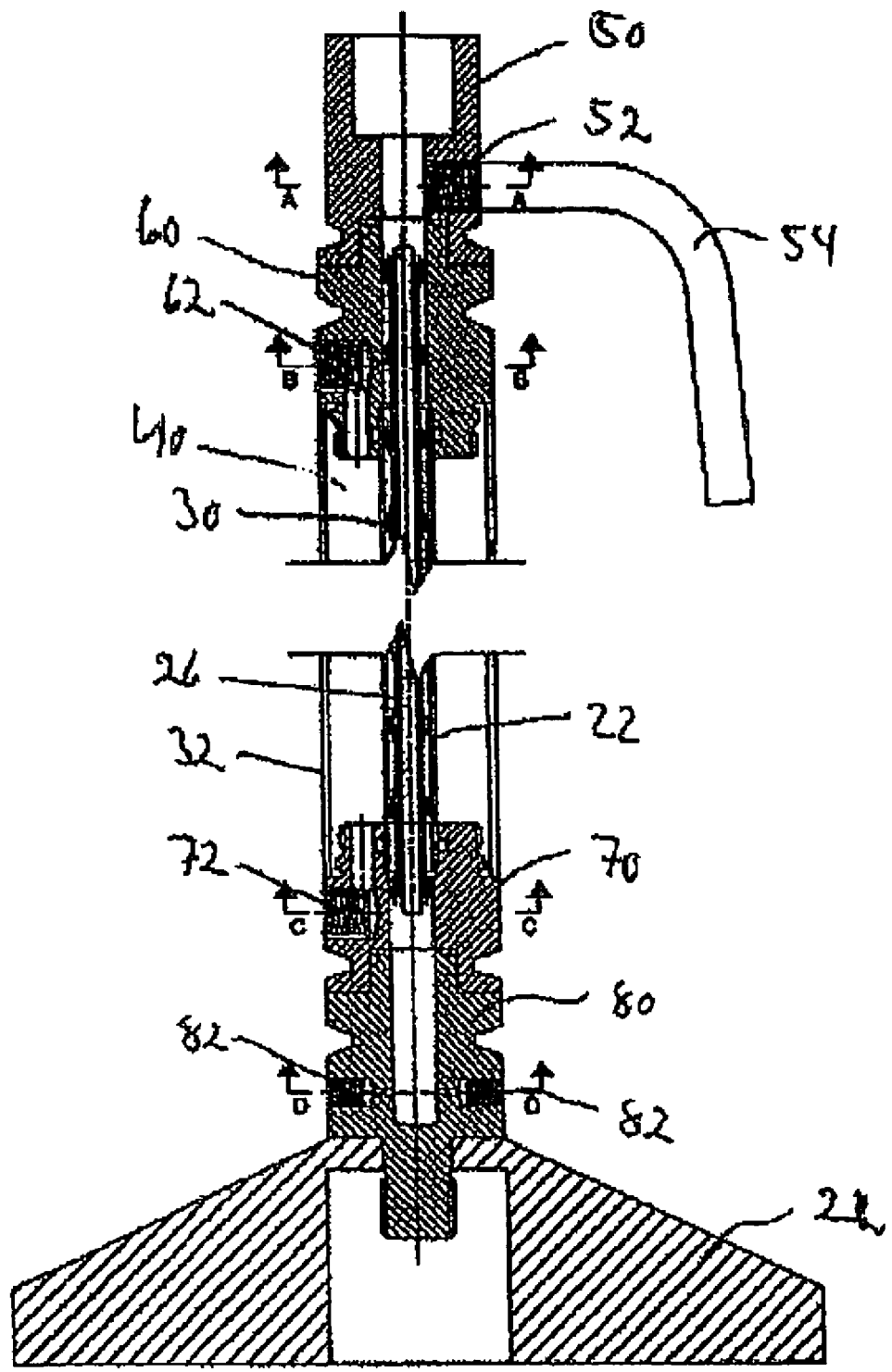
FIG. 2 shows a longitudinal section of a variant of a reactor.

The continuous preparations are conducted in a continuous flow reactor as shown in FIGS. 1 and 2, in which FIG. 1 shows a drawing of an embodiment example of a reactor, and FIG. 2 shows a longitudinal section of a variant of a reactor.

FIG. 1 shows a reactor 20 that is composed of several part components, where at least some of the components can be joined together with the help of one or more fastening connections, such as for example, a clamp connection 29. The different part components, or sections, encompass correspondingly shaped jointing parts so that the reactor can be put together with as many sections as is desirable. To drive an oscillator 26 in the reactor, a motor 28 or the like is arranged in the reactor adjoining the oscillator 26, where the oscillator 26, in connection with the motor 28, forces, in relation to at least one reactor chamber 22 in the reactor, a pulsating forward and backward movement of the oscillator 26. The motor 28 preferably has a speed regulator and the motor 28 is controlled so that the oscillator 26 pulsates at a predetermined and controllable amplitude and frequency. The reactor can also comprise a lower support foot 21, and also an upper product outlet pipe 54. Furthermore, the reactor 20 comprises externally a number of communication openings 64, 82 in the form of inlets and outlets for supply of reactants and outflow of products, respectively. The different fluids are fed into the reactor via the inlets and pumped through the reactor until they finally are led out through the outlets arranged preferably in the upper section of the reactor at the product outlet pipe 54.

In a preferred embodiment, the reactor can have a length in the area 5-300 cm, more preferably 50-200 cm, most preferably 80-150 cm, and the flow of fluid through the reactor can be 0.1-1000 ml/min.

Via a number of controlled pumps (not shown in detail in the Figures), different fluids are fed into the reactor 20. The reactor 20 can be of any shape imaginable, but a preferred embodiment of the reactor has a cylindrical shape as shown in the Figures. The diameter and length of the reactor can also be varied. One or more chemical compounds/reactants can be dissolved in separate solvents, or there can be one or several compounds in liquid phase, and the different fluids can be fed into the reactor with different fluid flow velocities controlled by the different pumps. The reactor can function in any position, but it is generally preferred that the reactor is arranged vertically, and that the different fluids are fed into the bottom section of the reactor, and that they are thus pumped against gravitational forces through the reactor, and that intermediate products or final products are led out at a higher level in the reactor.

The oscillator 26 is preferably shaped as a rod or strut comprising a number of ring-formed, external discs 30 arranged mutually spaced apart in the longitudinal direction of the oscillator, where the oscillator with the discs is inserted with a close fit in at least one chamber 22 of the reactor so that an annular reaction room 24 for conversion of chemical reactants is formed in the reactor, between the outer surface of the oscillator 26 and the internal surface 22 of the chamber. Said ring-formed discs 30 are fitted with a number of perforations 30*a* to permit through flow of fluid, and to contribute to the mixing of fluid in the chamber 22. When the oscillator is moved upward and downward, the fluids in the reactor 20 will be forced through the perforations 30*a* in the discs 30. It is this forcing of fluid through small perforations 30*a* that increases the through-flow velocity of the fluid for the different molecules in the fluid. The number of discs 30 in the reactor 20, and the number of perforations 30*a*, and the diameter of the perforations 30*a* will be decided according to the reaction that is carried out in the reactor 20. Typically, one will prefer a large number of discs, and also many small perforations.

The discs 30 can have a mutual centre-to-centre distance in the area 0.2 cm-3.0 cm, more preferably in the area 0.8-1.4 cm, and most preferably about 1 cm. Each disc 30 can be fitted with 1-10 perforations 30*a*, preferably 2-6 perforations, more preferably 3-5 perforations, and most preferably 4 perforations. Furthermore, each perforation 30*a* can have a diameter in the area 0.2-3 mm, more preferably in the area 0.5-2 mm, and most preferably about 1.25 mm.

The ratio between the area of the internal surface of the chamber 22 and the volume of the annular reaction room 24 can, for example, be in the area 1.5-35 $cm^2/cm^3$. Furthermore, the ratio between the area of the internal surface of the chamber 22 and the volume of the annular reaction room 24 can be more specifically in the area 5- 20 $cm^2/cm^3$. Alternatively the ratio between the area of the internal surface of the chamber 22 and the volume of the annular reaction room 24 can be about 10 $cm^2/cm^3$.

One of the issues that separate the present reactor from other previously known reactors is the ratio between "the volume that is available for chemical reaction" and "the contact surface that is available for contact between reactants/solvents and the heating/cooling medium". The reactor according to the present invention provides such a ratio between the heating/cooling surface and reaction volume that has not been previously available.

The invention claimed is:

1. A process for the preparation of 1,4-benzoquiones of formula (II)

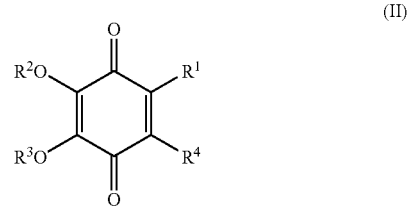

(II)

wherein $R^1$, $R^2$, $R^3$ and $R^4$ are independently selected from the group consisting of branched or unbranched $C_1$-$C_6$ alkyl, phenyl and benzyl, wherein phenyl and benzyl is optionally substituted by one or more substituent independently selected from the group consisting of $C_1$-$C_6$ alkyl and halogen, and wherein $C_1$-$C_6$ alkyl is optionally substituted with one or more halogen substituents, and wherein R2 and R3 together can form a $C_1$-$C_6$-alkylene radical, optionally substituted by one or more substituents independently selected from the group comprising $C_1$-$C_6$, benzyl, phenyl and halogen, by reacting a compound of formula (III)

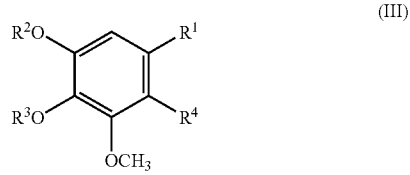

(III)

wherein $R^1$, $R^2$, $R^3$ and $R^4$ are as defined above, with a peroxide oxidant, in an acidic solvent, with the presence of an acid catalyst which is para-toluenesulfonic acid, wherein the process does not involve a Fenton type reagent.

2. A process in accordance with claim 1, wherein $R^1$ is methyl.

3. A process in accordance with claim 1, wherein $R^2$ is methoxy.

4. A process in accordance with claim 1, wherein $R^3$ is methoxy.

5. A process in accordance with claim 1, wherein $R^4$ is H.

6. A process in accordance with claim 1, wherein $R^1$ is methyl, $R^2$ and $R^3$ are methoxy, and $R^4$ is H or a halogen.

7. A process in accordance with claim 1, wherein $R^1$ is methyl, $R^2$ and $R^3$ are methoxy, and $R^4$ is H, i.e. 2,3-dimethoxy-5-methyl-[1,4]benzoquinone.

8. A process in accordance with claim 1, wherein the temperature is within the range of 0 to 100° C.

9. A process in accordance with claim 1 further comprising steps of; cooling the reaction mixture to 0-5° C., and adding $HNO_3$ in order to increase the yield of formula (II).

10. A compound having the formula (IV),

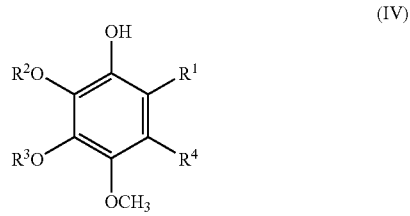

(IV)

wherein $R^1$, $R^2$, $R^3$ and $R^4$ are independently selected from the group consisting of branched or unbranched $C_1$-$C_6$ alkyl, phenyl and benzyl, wherein phenyl and benzyl is optionally substituted by one or more substituent independently selected from the group consisting of $C_1$-$C_6$ alkyl and halogen, and wherein $C_1$-$C_6$ alkyl is optionally substituted with one or more halogen substituents, and wherein R2 and R3 together can form a $C_1$-$C_6$-alkylene radical, optionally substituted by one or more substituents independently selected from the group comprising $C_1$-$C_6$, benzyl, phenyl and halogen.

11. A compound according to claim 10, wherein R1 is methyl, R2 and R3 are methoxy, and $R^4$ is H or a halogen.

12. A compound according to claim 10, wherein R1 is methyl, R2 and R3 are methoxy, and $R^4$ is H.

13. A compound having the formula (V)

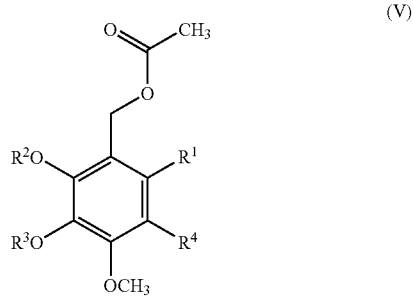

(V)

wherein $R^1$, $R^2$, $R^3$ and $R^4$ are independently selected from the group consisting of branched or unbranched $C_1$-$C_6$ alkyl, phenyl and benzyl, wherein phenyl and benzyl is optionally substituted by one or more substituent independently selected from the group consisting of $C_1$-$C_6$ alkyl and halogen, and wherein $C_1$-$C_6$ alkyl is optionally substituted with one or more halogen substituents, and wherein $R^2$ and $R^3$ together can form a $C_1$-$C_6$-alkylene radical, optionally substituted by one or more substituents independently selected from the group comprising $C_1$-$C_6$, benzyl, phenyl and halogen.

14. A compound according to claim 13, wherein $R^1$ is methyl, $R^2$ and $R^3$ are methoxy, and $R^4$ is H or a halogen.

15. A compound according to claim 13, wherein $R^1$ is methyl, $R^2$ and $R^3$ are methoxy, and $R^4$ is H.

16. A method for the preparation of coenzyme $Q_n$ of formula (VII)

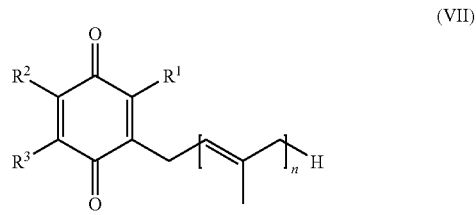

(VII)

Wherein a compound of the formula (II), $R^1$, $R^2$, $R^3$ and are as defined above, and $R^4$ is H,

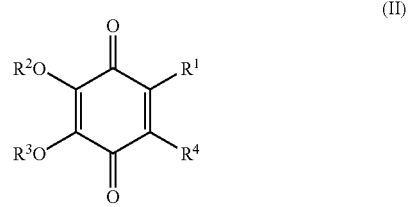

(II)

is prepared by reacting a compound of formula (III)

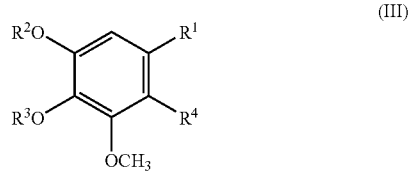

(III)

wherein $R^1$, $R^2$, $R^3$ and $R^4$ are as defined above, with a peroxide oxidant in an acidic solvent, with the presence of an acid catalyst which is para-toluenesulfonic acid, and then activating the compound of formula (II), and coupling the activated compound of formula (II) with a compound of formula (VIII)

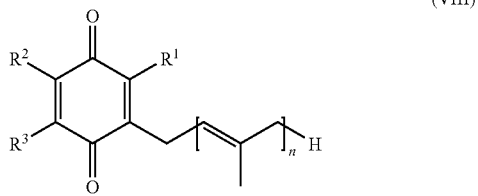

(VIII)

wherein the method does not involve a Fenton type reagent.

17. A process in accordance with claim 1, further comprising: continuously synthesizing said 1,4-benzoquiones with the formula (II) in a reactor that encompasses an annular reaction room for supply and outflow of reactants, wherein the reactants are fed from one end of the annular reaction room to the other to be forced through perforations in a number of discs arranged on an oscillator set up so that good mixing is obtained, and wherein a ratio between "the area of the internal surface of the reaction room" and "the volume of the annular reaction room" is in a range of 5-20 $cm^2/cm^3$.

18. A process in accordance with claim 1, wherein said peroxide oxidant is $H_2O_2$ and said acidic solvent is AcOH.

19. A process in accordance with claim 8, wherein the temperature is substantially 75° C.

20. A process in accordance with claim 9, wherein the cooling step lasts at least 10 minutes.

21. A method in accordance with claim 16, wherein said peroxide oxidant is $H_2O_2$ and said acidic solvent is AcOH.

22. A method in accordance with claim 17, wherein said peroxide oxidant is $H_2O_2$ and said acidic solvent is AcOH.

23. A method in accordance with claim 17, wherein the ratio is substantially 10 $cm^{2/}cm^3$.

* * * * *